(«12») United States Patent
Gewald et al.

(10) Patent No.: US 6,229,042 B1
(45) Date of Patent: May 8, 2001

(54) PROCESS FOR THE PREPARATION OF ENANTIOMERICALLY PURE 3-HYDROXY-OCTANEDIOIC ACID DIESTERS BY ASYMMETRIC CATALYTIC HYDROGENATION

(75) Inventors: Rainer Gewald, Dresden; Gunter Laban, Langerbrüch, both of (DE)

(73) Assignee: ASTA Medica Aktiengesellschaft (DE)

( * ) Notice: Subject to any disclaimer, the term of this patent is extended or adjusted under 35 U.S.C. 154(b) by 0 days.

(21) Appl. No.: 09/443,049

(22) Filed: Nov. 18, 1999

Related U.S. Application Data

(62) Division of application No. 09/035,811, filed on Mar. 6, 1998, now abandoned.

(30) Foreign Application Priority Data

Mar. 6, 1997 (DE) .................................. 19709069

(51) Int. Cl.⁷ .................................. C07C 69/99
(52) U.S. Cl. .................................. 560/180; 560/145
(58) Field of Search .................................. 560/180, 145

(56) References Cited

U.S. PATENT DOCUMENTS

| 3,883,580 | * | 5/1975 | Solodar | 560/164 |
| 4,772,727 | * | 9/1988 | Sutherland et al. | 549/39 |
| 4,916,252 | * | 4/1990 | Sayo et al. | 560/39 |
| 5,508,435 | * | 4/1996 | Armstrong, III et al. | 548/543 |

FOREIGN PATENT DOCUMENTS

0295109 * 12/1988 (EP) .

OTHER PUBLICATIONS

Sato et al, Use of 1,3–dioxin–4 ones and Related Compounds in Synthesis, J. Am. Chem. Soc., p. 4279–87, Apr. 1995.*

* cited by examiner

*Primary Examiner*—Paul J. Killos
*Assistant Examiner*—Taylor V. Oh
(74) *Attorney, Agent, or Firm*—Pillsbury Madison & Sutro LLP

(57) ABSTRACT

The invention relates to a process for the preparation of compounds of the general formula I

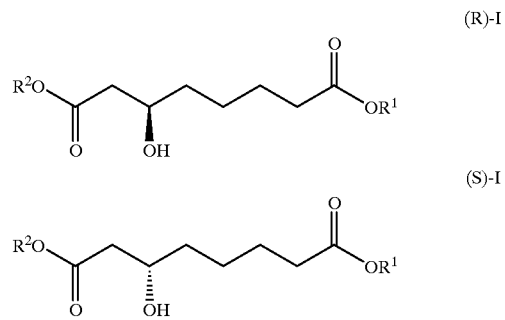

in which $R^1$ and $R^2$ are identical or different and are a $C_1$–$C_{20}$-alkyl group, $C_3$–$C_{12}$-cycloalkyl group, $C_7$–$C_{12}$-aralkyl group or a mono- or binuclear aryl group, in which a ketone of the formula III or IV

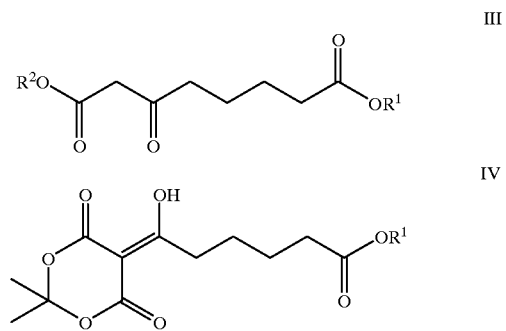

in which $R^1$ and $R^2$ have the above meaning, is asymmetrically hydrogenated.

1 Claim, No Drawings

PROCESS FOR THE PREPARATION OF ENANTIOMERICALLY PURE 3-HYDROXY-OCTANEDIOIC ACID DIESTERS BY ASYMMETRIC CATALYTIC HYDROGENATION

This is a division of application Ser. No. 09/035,811 filed Mar. 6, 1998 now abandoned.

The present invention relates to a novel process for the preparation of enantiomerically pure 3-hydroxyoctanedioic acid diesters of the general formula I, where $R^1$ and $R^2$ are identical or different and are a $C_1$–$C_{20}$-alkyl group, $C_3$–$C_{12}$-cycloalkyl group, $C_7$–$C_{12}$-aralkyl group or a mono- or binuclear aryl group.

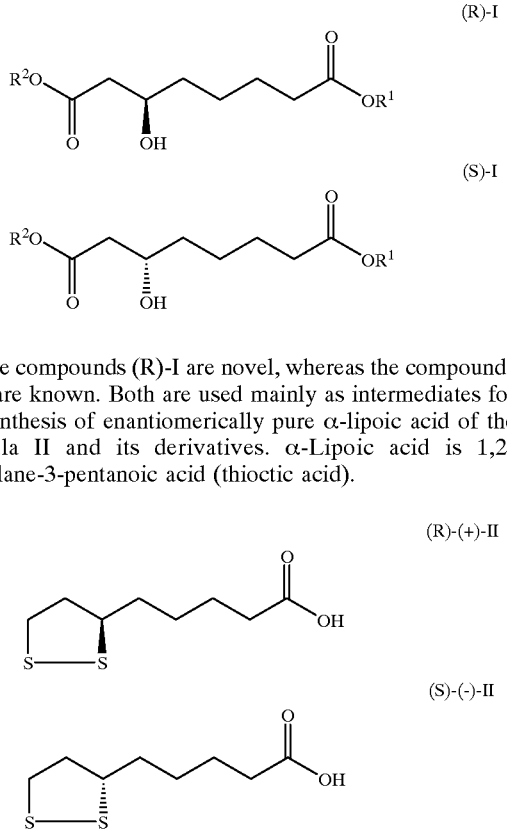

The compounds (R)-I are novel, whereas the compounds (S)-I are known. Both are used mainly as intermediates for the synthesis of enantiomerically pure α-lipoic acid of the formula II and its derivatives. α-Lipoic acid is 1,2-dithiolane-3-pentanoic acid (thioctic acid).

The (R)-enantiomer of α-lipoic acid (R)-(+)-II is a natural substance which occurs in low concentrations in virtually all animal and plant cells. As a coenzyme in the oxidative decarboxylation of α-ketocarboxylic acids (e.g. pyruvic acid), α-lipoic acid is of essential importance. α-Lipoic acid is pharmacologically active and has anti-inflammatory and antinociceptive (analgesic) and cytoprotective properties. An important medical indication is the treatment of diabetic polyneuropathy. According to recent results (A. Baur et al., Klin. Wochenschr. 1991, 69, 722; J. P. Merin et al., FEBS Lett. 1996, 394, 9), α-lipoic acid may possibly gain importance in the control of diseases caused by HIV-1 and HTLV IIIB viruses.

In the case of the pure optical isomers of α-lipoic acid (R- and S-form, i.e. (R)-α-lipoic acid and (S)-α-lipoic acid), unlike the racemate, the (R)-enantiomer mainly has anti-inflammatory activity and the (S)-enantiomer mainly antinociceptive activity (EP 0427247, 08.11.90). Different pharmacokinetic properties of the two enantiomers have likewise been found (R. Hermann et al., Eur. J. Pharmaceut. Sci. 1996, 4, 167). The synthesis of the pure enantiomers is therefore of great importance.

Known preparation processes for the enantiomerically pure α-lipoic acids include the resolution of the racemates of α-lipoic acid or its precursors, asymmetric syntheses using chiral auxiliaries, "chiral pool" syntheses using naturally occurring optically active starting compounds and microbial syntheses (review article: J. S. Yadav et al., J. Sci. Ind. Res. 1990, 49, 400; and also: E. Walton et al., J. Am. Chem. Soc. 1955, 77, 5144; D. S. Acker and W. J. Wayne, J. Am. Chem. Soc. 1957, 79, 6483; L. G. Chebotareva and A. M. Yurkevich, Khim.-Farm. Zh. 1980, 14, 92; A. S. Gopalan et al., Tetrahedron Lett. 1989, 5705; A. G. Tolstikov et al., Bioorg. Khim. 1990, 16, 1670; L. Dasaradhi et al., J. Chem. Soc., Chem. Commun. 1990, 729; A. S. Gopalan et al., J. Chem. Perkin Trans. 1 1990, 1897; EP 0487986 A2, 14.11.91; B. Adger et al., J. Chem. Soc., Chem. Commun. 1995, 1563; Y. R. Santosh Laxmi and D. S. Iyengar, Synthesis, 1996, 594).

Of these, the resolution of the racemate via the formation of diastereomeric salts of α-lipoic acid with optically active a-methylbenzylamine (DE-A 4137773.7, 16.11.91 and DE-A 4427079.8, 30.07.94) represents the most economical variant up to now. Since the racemate separation only takes place in the last stage of the synthesis sequence, however, high yields cannot be attained.

The only known chemocatalytic asymmetric process for the preparation of enantiomerically pure α-lipoic acid (DE-A 3629116.1, 27.08.86) is based on the Sharpless epoxidation of allyl alcohols, but is uneconomical because of the high costs of the starting compounds.

Among the biocatalytic synthesis routes described, the asymmetric reduction of 3-oxooctanedioic acid diesters III with baker's yeast is to be emphasized (EP 0487986 A2, 14.11.91). The disadvantages of this process, however, are that the space-time yield is extremely low, a high enantiomeric excess can only be achieved when using the isobutyl ester ($R^1$=iBu) and always only the (S)-enantiomer (S)-I is formed.

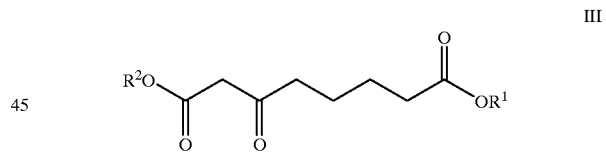

The object of the invention is therefore alternatively to make both enantiomers of α-lipoic acid available in high chemical and optical space-time yield when using inexpensive starting substances. According to the invention, this is achieved by asymmetric chemocatalytic hydrogenation of 3-oxooctanedioic acid diesters of the formula III, in which $R^1$ and $R^2$ in each case independently of one another are a $C_1$–$C_{20}$-alkyl group, $C_3$–$C_{12}$-cycloalkyl group, $C_7$–$C_{12}$-aralkyl group or a mono- or binuclear aryl group, in the presence of complexes of ruthenium and optically active phosphines or of Raney nickel and optically active tartaric acid as catalysts.

In this case, independently of the nature of the ester groups ($R^1$, $R^2$), constant high optical and chemical yields of 3-hydroxyoctanedioic acid diesters I are attained. Unlike the biocatalytic variants, the reaction can be carried out at very high substrate concentrations.

The compounds III are known and obtainable especially by acylation of Meldrum's acid with monoalkyl adipoyl chloride and subsequent alcoholysis (H. Thoma and G. Spiteller, Liebigs Ann. Chem. 1983, 1237; EP 0487986 A2, 14.11.91). Under certain reaction conditions, according to the invention preferably also the alkyl 6-(2,2-dimethyl-4,6-dioxo-1,3-dioxan-5-ylidene) 6-hydroxyhexanoates of the formula IV ($R^1=C_1$–$C_{20}$-alkyl, $C_3$–$C_{12}$-cycloalkyl, $C_7$–$C_{12}$-aralkyl and/or mono- or binuclear aryl) which are intermediately formed and can be isolated can be used for the asymmetric hydrogenation. They can be prepared as described (H. W. Schmidt and M. Klade, Org. Prep. Proced. Int. 1988, 20, 184) or prepared in an analogous manner.

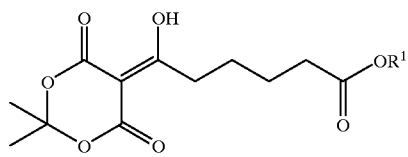

IV

Of particular interest as catalysts for the asymmetric hydrogenation are ruthenium-diphosphine complexes. As typical examples but not as a restriction, the ruthenium complexes of the following formulae V to XI may be mentioned:

| | |
|---|---|
| [RuHal$_2$D]$_{1,2}$(L)$_x$ | V |
| [RuHalAD]$^+$Y$^-$ | VI |
| RuD$_n$OOCR$^3$OOCR$^4$ | VII |
| [RuH$_x$D$_n$]$^{m+}$Y$_m^-$ | VIII |
| [RuHal(PR$^5{}_2$R$^6$)D)]$^{2+}$Hal$_2^-$ | IX |
| [RUHHalD$_2$] | X |
| [DRu(acac)$_2$] | XI | in which:
acac is acetylacetonate,
D is a diphosphine of the general formula XII,
Hal is halogen, in particular iodine, chlorine or bromine,
$R^3$ and $R^4$ are identical or different and are alkyl having up to 9 C atoms, preferably up to 4 C atoms, which is optionally substituted by halogen, in particular fluorine, chlorine or bromine or are phenyl which is optionally substituted by alkyl having 1 to 4 C atoms or are α-aminoalkanoic acid preferably having up to 4 C atoms, or jointly form an alkylidene group having up to 4 C atoms,
$R^5$ and $R^6$ in each case are identical or different and are optionally substituted phenyl, preferably substituted by alkyl having 1 to 4 C atoms or halogen,
Y is Cl, Br, I, ClO$_4$, BF$_4$ or PF$_4$,
A is an unsubstituted or substituted benzene ring such as p-cymene,
L is a neutral ligand such as acetone, a tertiary amine or dimethylformamide,
n and m in each case are 1 or 2,
x is 0 or 1,
where in formula VIII n is 1 and m is 2 if x=0, and n is 2 and m is 1 if x=1.

The complexes of the formulae V to XI can be prepared by methods known per se (V and X: EP 174057 and J. P.Genet et al., Tetrahedron Asymmetry 1994, 5, 675; VI: EP 366390; VII: EP 245959 and EP 272787; VIII: EP 256634; IX: EP 470756; XI: P. Stahly et al., Organometallics 1993, 1467).

Optically active diphosphine ligands which can be used are compounds of the general formula XII:

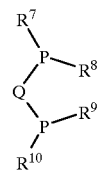

XII in which:

Q is a group bridging the two P atoms having 2 to 24 carbon atoms and optionally 1 to 4 heteroatoms, preferably O, S, N and Si, the bridge being formed by at least 2 of the carbon atoms and optionally 1 to 4 of the heteroatoms, $R^7$–$R^{10}$ in each case are identical or different and are alkyl groups having 1 to 18 C atoms, cycloalkyl groups having 5 to 7 C atoms or aryl groups having 6 to 12 C atoms.

As particularly preferred chiral diphosphines which can be used in enantiomerically pure form, the following ligands can be mentioned as examples:

The ligands mentioned above as racemic structures for the sake of simplicity are known compounds in their enantiomerically pure forms (BINAP: R. Noyori et al., J. Am. Chem. Soc. 1980, 102, 7932; BIMOP, FUPMOP, BIFUP: M. Murata et al., Synlett 1991, 827; BIBHEMP: R. Schmid et al., Helv. Chim. Acta 1988, 71, 697; MeO-BIPHEP: R. Schmid et al., Helv. Chim. Acta 1991, 74, 370; BICHEP: A. Miyashita et al., Chem. Lett. 1989, 1849; DuPHOS: M. Burk et al., Organometallics 1990, 9, 2653; BPE: M. Burk et al., J. Am. Chem. Soc. 1995, 117, 4423; BIBFUP: EP 643065; CHIRAPHOS: B. Bosnich et al., J. Am. Chem. Soc. 1977, 99, 6262; XIII: WO 96/01831).

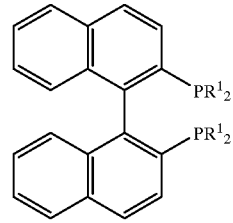

BINAP: $R^1$ = Phenyl
Tolyl-BINAP: $R^1$ = p-Tolyl

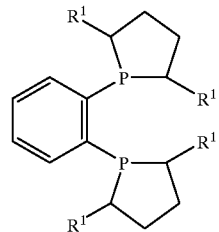

Me-DuPHOS: $R^1$ = Me
Et-DuPHOS: $R^1$ = Et

-continued

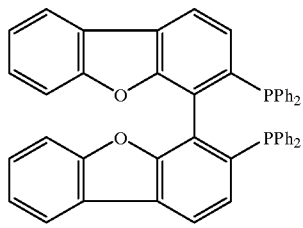

BIBFUP

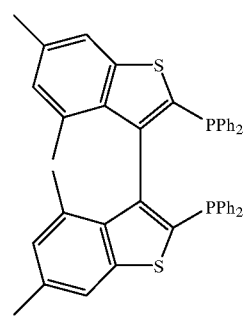

XIII

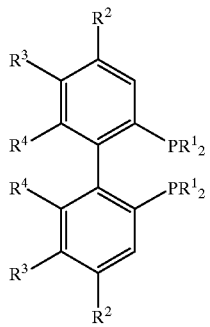

BIMOP: $R^1$ = Ph, $R^2$ = $R^4$ = Me, $R^3$ = OMe
FUPMOP: $R^1$ = Ph, $R^2$ = $R^4$ = CF$_3$, $R^3$ = OMe
BIFUP: $R^1$ = Ph, $R^2$ = $R^4$ = CF$_3$, $R^3$ = H
BIPHEMP: $R^1$ = Ph, $R^2$ = $R^3$ = H, $R^4$ = Me
MeO-BIPHEP: $R^1$ = Ph, $R^2$ = $R^3$ = H, $R^4$ = OMe
BICHEP: $R^1$ = c-C$_6$H$_{11}$, $R^2$ = $R^3$ = H, $R^4$ = Me

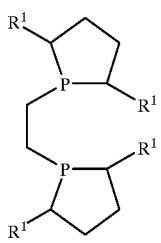

Me-BPE: $R^1$ = Me
iPr-BPE: $R^1$ = iPr

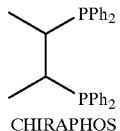

CHIRAPHOS

The asymmetric hydrogenation of the compounds of the formula III in the presence of the optically active ruthenium-diphosphine complexes of the formulae V to XI described above can be carried out in suitable organic solvents which are inert under the reaction conditions. Those which can be mentioned in particular are alcohols such as methanol or ethanol, chlorinated hydrocarbons such as methylene chloride or dichloroethane, cyclic ethers such as tetrahydrofuran or dioxane, esters such as, for example, ethyl acetate, aromatic hydrocarbons such as benzene or toluene, or alternatively mixtures thereof and the like. To suppress possible ketal formation when working in alcohols as solvents, up to 10% by volume of water can be added. The substrate concentrations are preferably 5 to 50% by volume, in particular 20 to 40% by volume.

The reactions can preferably be carried out at temperatures from approximately 10° C. to 120° C., in particular from approximately 20° C. to 70° C. and under a hydrogen pressure from approximately 1 to 100 bar, in particular from 4 to 50 bar. In general, the reaction times are 2 to 48 hours, usually 6 to 24 hours. The molar ratio between ruthenium in the complexes V to XI and the compounds III to be hydrogenated is expediently between approximately 0.001 and approximately 5 mol %, preferably between approximately 0.005 and approximately 0.2 mol %.

Under the abovementioned conditions, according to the invention compounds of the formula IV can also be asymmetrically hydrogenated in the presence of the optically active ruthenium-diphosphine complexes of the formulae V to XI, the reaction preferably being carried out in alcohols or mixtures of the abovementioned organic solvents and at least 1, preferably 4 to 10, mol of alcohol, based on the compound IV to be hydrogenated, and at temperatures from approximately 40° C. to 120° C., in particular from approximately 50° C. to 100° C. In the reaction products I, the radical $R^2$ is then defined by the corresponding alcohol employed.

In the reaction, the desired enantiomer of the formula I can be obtained by selection of the optically active diphosphine ligands of the formula XII with the appropriate configuration. Thus, for example, the use of (R)-(+)-BINAP leads to products of the formula (R)-I, the use of (S)-(−)-BINAP to products of the formula (S)-I.

According to the invention, chirally modified Raney nickel complexes can also be used as catalysts for the asymmetric hydrogenation. These complexes can be prepared by methods known per se (T. Harada et al., Bull. Chem. Soc. Jpn. 1994, 67, 2473; A. Tai et al., J. Chem. Soc., Chem. Commun. 1991, 795; H. Brunner et al., Tetrahedron: Asymmetry 1990, 1, 159; T. Harada et al., Chem. Lett. 1980, 1125; T. Harada and Y. Izumi, Chem. Lett. 1978, 1195). In this case, Raney nickel complexes treated with enantiomerically pure tartaric acid with addition of sodium bromide prove to be particularly suitable, ultrasonically treated Raney nickel being preferably employed for the formation of the catalyst complex.

The asymmetric hydrogenation of the compounds of the formula III in the presence of the optically active nickel-tartaric acid complexes described above can be carried out in suitable organic solvents which are inert under the reaction conditions. Those which can be mentioned in particular are alcohols such as methanol or ethanol, chlorinated hydrocarbons such as methylene chloride or dichloroethane, cyclic ethers such as tetrahydrofuran or dioxane, esters such as, for example, ethyl acetate or propionic acid esters, aromatic hydrocarbons such as benzene or toluene, or alternatively mixtures thereof and the like. The solvent or solvent mixture used can contain up to 10% by volume, preferably 0.05 to 2% by volume, of a carboxylic acid, in particular acetic acid. The substrate concentrations are preferably 5 to 60% by volume, in particular 30 to 50% by volume.

The reactions can preferably be carried out at temperatures from approximately 20° C. to 140° C., in particular from approximately 70° C. to 100° C. and under a hydrogen pressure from approximately 1 to 100 bar, in particular from 20 to 80 bar. In general, the reaction times are 2 to 48 hours, usually 6 to 36 hours. The molar ratio between nickel in the complexes and the compounds III to be hydrogenated is expediently between approximately 0.01 and approximately 50 mol %, preferably between approximately 1 and approximately 20 mol %.

Under the abovementioned conditions, according to the invention compounds of the formula IV can also be asymmetrically hydrogenated in the presence of the optically active nickel-tartaric acid complexes, the reaction preferably being carried out in alcohols or mixtures of abovementioned organic solvents and at least 1, preferably 4 to 10, mol of alcohol, based on the compound to be hydrogenated. In the reaction products I, the radical $R^2$ is then defined by the corresponding alcohol employed.

In the reaction, the desired enantiomer of the formula I can be obtained by selection of the optically active tartaric acid with the appropriate configuration in the preparation of the catalyst complex. Thus the use of (R,R)-(+)-tartaric acid leads to products of the formula (R)-I, the use of (S,S)-(−)-tartaric acid to products of the formula (S)-I.

The compounds I are used for the preparation of the enantiomerically pure α-lipoic acids of the formula II, by reducing them in a known manner (EP 0487986 A2, 14.11.91) to the compounds XIV, where $R^1$ is a $C_1$–$C_{20}$-alkyl group, $C_3$–$C_{12}$-cycloalkyl group, $C_7$–$C_{12}$-aralkyl group or a mono- or binuclear aryl group

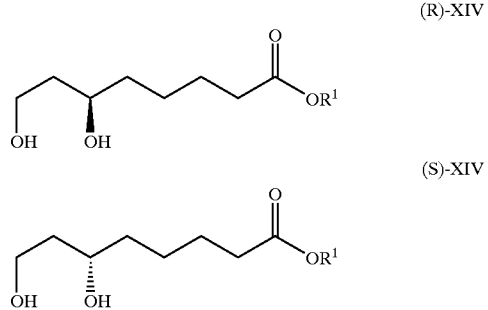

and these
a) are converted into the bis-sulphonic acid ester of XIV in organic solution using a sulphonyl chloride and a tertiary nitrogen base,
b) this compound is reacted in a polar solvent with sulphur and an alkali metal sulphide to give the α-lipoic acid ester and
c) this ester is converted, if desired, into the respective pure enantiomer of α-lipoic acid. In this case, starting from the compounds (R)-I (S)-(−)-α-lipoic acid and, starting from the compounds (S)-I, (R)-(+)-α-lipoic acid is obtained.

The compounds (R)-I and (S)-I and also (R)-(+)-II and (S)-(−)-II prepared by the processes according to the invention as a rule have a high enantiomeric excess, corresponding to an optical yield of 70 to 99%.

The enantiomer ratios are measured directly by means of chiral HPLC on optically active columns.

The present invention enables the enantiomerically pure 3-hydroxyoctanedioic acid diesters of the general formula I ($R^1$, $R^2$=$C_1$–$C_{20}$-alkyl, $C_3$–$C_{12}$-cycloalkyl, $C_7$–$C_{12}$-aralkyl and/or mono- or binuclear aryl) to be made available in an economical manner in high chemical and optical yields as intermediates for the preparation of the enantiomerically pure α-lipoic acids of the formula II.

The following examples illustrate the invention without restricting it.

Example 1

43.5 mg (0.087 mmol) of [$RuCl_2$ ($C_6H_6$)]$_2$, 113.7 mg (0.183 mmol) of (R)-BINAP and 3 ml of dimethylformamide were added under argon to a 20 ml Schlenk vessel. The reddish-brown suspension was heated to 100° C. for 10 min. The now clear solution was cooled and concentrated in vacuo (1 to 0.1 mm Hg) at 50° C. with vigorous stirring over a period of 1 h. The remaining orange-brown solid was taken up in 1 ml of tetrahydrofuran and was used thus in the asymmetric hydrogenations as an Ru-(R)-BINAP catalyst.

Example 2

43.5 mg (0.087 mmol) of [$RuCl_2$ ($C_6H_6$)]$_2$, 113.7 mg (0.183 mmol) of (S)-BINAP and 3 ml of dimethylformamide were added under argon to a 20 ml Schlenk vessel. The reddish-brown suspension was heated to 100° C. for 10 min. The now clear solution was cooled and concentrated in vacuo (1 to 0.1 mm Hg) at 50° C. with vigorous stirring over a period of 1 h. The remaining orange-brown solid was taken up in 1 ml of tetrahydrofuran and was used thus in the asymmetric hydrogenations as an Ru-(S)-BINAP catalyst.

Example 3

43.5 mg (0.087 mmol) of [$RUCl_2$ ($C_6H_6$)]$_2$, 124.2 mg (0.183 mmol) of (R)-tolyl-BINAP and 3 ml of dimethylformamide were added under argon to a 20 ml Schlenk vessel. The reddish-brown suspension was heated to 100° C. for 10 min. The now clear solution was cooled and concentrated in vacuo (1 to 0.1 mm Hg) at 50° C. with vigorous stirring over a period of 1 h. The remaining orange-brown solid was taken up in 1 ml of tetrahydrofuran and was used thus in the asymmetric hydrogenations as an Ru-(R)-tolyl-BINAP catalyst.

Example 4

A 100 ml autoclave was loaded under argon with 21.6 g (0.1 mol) of dimethyl 3-oxooctanedioate, with the Ru-(R)-BINAP catalyst solution prepared under Example 1 and with 40 ml of oxygen-free methanol. The hydrogenation was carried out for 20 hours at 60° C., a constant pressure of 40 bar of pure $H_2$ and with intensive stirring. After completion of the reaction, the solvent was distilled off on a rotary evaporator. 21.2 g (97%) of dimethyl (R)-3-hydroxyoctanedioate (content: 96%) having an enantiomeric excess of 98% (chiral HPLC) were obtained.

Example 5

A 100 ml autoclave was loaded under argon with 21.6 g (0.1 mol) of dimethyl 3-oxooctanedioate, with the Ru-(S)-BINAP catalyst solution prepared under Example 2 and with 40 ml of oxygen-free methanol. The hydrogenation was carried out for 20 hours at 65° C., a constant pressure of 35 bar of pure $H_2$ and with intensive stirring. After completion of the reaction, the solvent was distilled off on a rotary evaporator. 21.3 g (98%) of dimethyl (S)-3-hydroxyoctanedioate (content: 97%) having an enantiomeric excess of 98% (chiral HPLC) were obtained.

Example 6

A 100 ml autoclave was loaded under argon with 21.6 g (0.1 mol) of dimethyl 3-oxooctanedioate, with the Ru-(R)- tolyl-BINAP catalyst solution prepared under Example 3 and with 40 ml of oxygen-free methanol. The hydrogenation was carried out for 20 hours at 65° C., a constant pressure of 40 bar of pure $H_2$ and with intensive stirring. After completion of the reaction, the solvent was distilled off on a rotary evaporator. 21.2 g (97%) of dimethyl (R)-3-hydroxyoctanedioate (content: 97%) having an enantiomeric excess of 97% (chiral HPLC) were obtained.

Example 7

A 100 ml autoclave was loaded under argon with 14.3 g (0.05 mol) of methyl 6-(2,2-dimethyl-4,6-dioxo-1,3-dioxan-5-ylidene)-6-hydroxyhexanoate, with the Ru-(R)-BINAP catalyst solution prepared under Example 1 and with 40 ml of oxygen-free methanol. The hydrogenation was carried out for 20 hours at 70° C., a constant pressure of 50 bar of pure $H_2$ and with intensive stirring. After completion of the reaction, the solvent was distilled off on a rotary evaporator. 10.4 g (95%) of dimethyl (R)-3-hydroxyoctanedioate (content: 96%) having an enantiomeric excess of 97% (chiral HPLC) were obtained.

Example 8

A 100 ml autoclave was loaded under argon with 14.3 g (0.05 mol) of methyl 6-(2,2-dimethyl-4,6-dioxo-1,3-dioxan-5-ylidene)-6-hydroxyhexanoate, with the Ru-(R)-BINAP catalyst solution prepared under Example 1 and with 40 ml of oxygen-free ethanol. The hydrogenation was carried out for 20 hours at 70° C., a constant pressure of 50 bar of pure $H_2$ and with intensive stirring. After completion of the reaction, the solvent was distilled off on a rotary evaporator. 11.1 g (96%) of 1-ethyl 8-methyl (R)-3-hydroxyoctanedioate (content: 95%) having an enantiomeric excess of 98% (chiral HPLC) were obtained.

Example 9

A 100 ml autoclave was loaded under argon with 24.4 g (0.1 mol) of diethyl 3-oxooctanedioate, with the Ru-(S)-BINAP catalyst solution prepared under Example 2 and with 40 ml of oxygen-free methanol. The hydrogenation was carried out for 24 hours at 60° C., a constant pressure of 30 bar of pure $H_2$ and with intensive stirring. After completion of the reaction, the solvent was distilled off on a rotary evaporator. 23.9 g (97%) of diethyl (S)-3-hydroxyoctanedioate (content: 98%) having an enantiomeric excess of 98% (chiral HPLC) were obtained.

Example 10

A 100 ml autoclave was loaded under argon with 24.4 g (0.1 mol) of 1-isopropyl 8-methyl 3-oxooctanedioate, with the Ru-(R)-BINAP catalyst solution prepared under Example 1 and with 40 ml of oxygen-free methanol. The hydrogenation was carried out at 55° C., a constant pressure of 60 bar of pure $H_2$ and with intensive stirring for 16 hours. After completion of the reaction, the solvent was distilled off on a rotary evaporator. 24.1 g (98%) of 1-isoproyl 8-methyl (R)-3-hydroxyoctanedioate (content: 97%) having an enantiomeric excess of 98% (chiral HPLC) were obtained.

Example 11

A 100 ml autoclave was loaded under argon with 25.8 g (0.1 mol) of 1-isobutyl 8-methyl 3-oxooctanedioate, with the Ru-(R)-BINAP catalyst solution prepared under Example 1 and with 40 ml of oxygen-free methanol. The hydrogenation was carried out at 100° C., a constant pressure of 5 bar of pure $H_2$ and with intensive stirring for 6 hours. After completion of the reaction, the solvent was distilled off on a rotary evaporator. 25.5 g (98%) of 1-isobutyl 8-methyl (R)-3-hydroxyoctanedioate (content: 96%) having an enantiomeric excess of 97% (chiral HPLC) were obtained.

Example 12

Raney nickel (W1 type) prepared from 3.8 g of an Ni/Al alloy (Ni/Al - 42/58) was treated in a glass flask for 3 min. in an ultrasonic bath (48 kHz) after addition of 40 ml of water. The supernatant turbid solution was decanted off by immobilizing the paramagnetic nickel on the bottom of the vessel with the aid of a magnet. This process was repeated twice.

2.4 g of (R,R)-(+)-tartaric acid and 24 g of sodium bromide were dissolved in 240 ml of water and the solution was adjusted to pH=3.2 by addition of 1M NaOH. The solution was then heated in a boiling water bath.

Half of the hot solution was added to the ultrasonically-treated Raney nickel and kept at 100° C. for 30 min. The supernatant solution was then decanted off and the catalyst complex was washed with 20 ml of water. The catalyst complex was then again suspended in the other half of the (R,R)-(+)-tartaric acid/sodium bromide solution and treated as described before. The supernatant solution was then decanted off and the catalyst complex was washed twice each with 20 ml of water, 20 ml of methanol, 20 ml of tetrahydrofuran and 20 ml of the solvent used in the hydrogenation. The (R,R)-(+)-tartaric acid-Raney nickel catalyst complex thus obtained was employed in the asymmetric hydrogenations as a suspension in the respective solvent.

Example 13

Raney nickel (W1 type) prepared from 3.8 g of an Ni/Al alloy (Ni/Al - 42/58) was treated in a glass flask for 3 min. in an ultrasonic bath (48 kHz) after addition of 40 ml of water. The supernatant turbid solution was decanted off by immobilizing the paramagnetic nickel on the bottom of the vessel with the aid of a magnet. This process was repeated twice.

2.4 g of (S,S)-(−)-tartaric acid and 24 g of sodium bromide were dissolved in 240 ml of water and the solution was adjusted to pH=3.2 by addition of 1M NaOH. The solution was then heated in a boiling water bath.

Half of the hot solution was added to the ultrasonically-treated Raney nickel and kept at 100° C. for 30 min. The supernatant solution was then decanted off and the catalyst complex was washed with 20 ml of water. The catalyst complex was then again suspended in the other half of the (S,S)-(−)-tartaric acid/sodium bromide solution and treated as described before. The supernatant solution was then decanted off and the catalyst complex was washed twice each with 20 ml of water, 20 ml of methanol, 20 ml of tetrahydrofuran and 20 ml of the solvent used in the hydrogenation. The (S,S)-(−)-tartaric acid-Raney nickel catalyst complex thus obtained was employed in the asymmetric hydrogenations as a suspension in the respective solvent.

Example 14

A 100 ml autoclave was loaded with 10.8 g (0.05 mol) of dimethyl 3-oxooctanedioate, with 0.9 g of the (R,R)-(+)-tartaric acid-Raney nickel catalyst prepared under Example 12, with 25 ml of methyl propionate and with 0.25 ml of acetic acid. The hydrogenation was carried out at 80° C., a constant pressure of 65 bar of pure $H_2$ and with intensive stirring for 24 hours. After completion of the reaction, 50 ml of diethyl ether were added, the catalyst complex was separated off by filtration, the filtrate was washed with aqueous sodium carbonate solution and the solvent was distilled off on a rotary evaporator. 10.6 g (97%) of dimethyl (R)-3-hydroxyoctanedioate (content: 98%) having an enantiomeric excess of 88% (chiral HPLC) were obtained.

Example 15

A 100 ml autoclave was loaded with 10.8 g (0.05 mol) of dimethyl 3-oxooctanedioate, with 0.9 g of the (S,S)-(−)-tartaric acid-Raney nickel catalyst prepared under Example 13, with 25 ml of methyl propionate and with 0.25 ml of acetic acid. The hydrogenation was carried out at 90° C., a constant pressure of 60 bar of pure H and with intensive stirring for 18 hours. After completion of the reaction, 50 ml of diethyl ether were added, the catalyst complex was separated off by filtration, the filtrate was washed with aqueous sodium carbonate solution and the solvent was distilled off on a rotary evaporator. 10.7 g (98%) of dimethyl (S)-3-hydroxyoctanedioate (content: 97%) having an enantiomeric excess of 89% (chiral HPLC) were obtained.

Example 16

A 100 ml autoclave was loaded with 11.5 g (0.05 mol) of 1-ethyl 8-methyl 3-oxooctanedioate, with 0.9 g of the (R,R)-(+)-tartaric acid-Raney nickel catalyst prepared under Example 12, with 25 ml of methyl propionate and with 0.25 ml of acetic acid. The hydrogenation was carried out at 90° C., a constant pressure of 75 bar of pure $H_2$ and with intensive stirring for 18 hours. After completion of the reaction, 50 ml of diethyl ether were added, the catalyst complex was separated off by filtration, the filtrate was washed with aqueous sodium carbonate solution and the solvent was distilled off on a rotary evaporator. 11.2 g (97%) of 1-ethyl 8-methyl (R)-3-hydroxyoctanedioate (content: 98%) having an enantiomeric excess of 85% (chiral HPLC) were obtained.

Example 17

A 100 ml autoclave was loaded with 12.2 g (0.05 mol) of diethyl 3-oxooctanedioate, with 0.9 g of the (S,S)-(−)-tartaric acid-Raney nickel catalyst prepared under Example 13, with 25 ml of methyl propionate and with 0.25 ml of acetic acid. The hydrogenation was carried out at 80° C., a constant pressure of 50 bar of pure $H_2$ and with intensive stirring for 24 hours. After completion of the reaction, 50 ml of diethyl ether were added, the catalyst complex was separated off by filtration, the filtrate was washed with aqueous sodium carbonate solution and the solvent was distilled off on a rotary evaporator. 11.9 g (97%) of diethyl (S)-3-hydroxyoctanedioate (content: 97%) having an enantiomeric excess of 86% (chiral HPLC) were obtained.

Example 18

A 100 ml autoclave was loaded with 14.3 g (0.05 mol) of methyl 6-(2,2-dimethyl-4,6-dioxo-1,3-dioxan-5-ylidene)-6-hydroxyhexanoate, with 1.9 g of the (R,R)-(+)-tartaric acid-Raney nickel catalyst prepared under Example 12, with 25 ml of ethyl acetate and with 5 ml of methanol. The hydrogenation was carried out at 90° C., a constant pressure of 80 bar of pure $H_2$ and with intensive stirring for 24 hours. After completion of the reaction, 50 ml of diethyl ether were added, the catalyst complex was separated off by filtration, the filtrate was washed with aqueous sodium carbonate solution and the solvent was distilled off on a rotary evaporator. 10.4 g (95%) of dimethyl (R)-3-hydroxyoctanedioate (content: 95%) having an enantiomeric excess of 82% (chiral HPLC) were obtained.

Example 19

A 100 ml autoclave was loaded with 14.3 g (0.05 mol) of methyl 6-(2,2-dimethyl-4,6-dioxo-1,3-dioxan-5-ylidene)-6-hydroxyhexanoate, with 1.9 g of the (S,S)-(−)-tartaric acid-Raney nickel catalyst prepared under Example 13, with 25 ml of ethyl acetate and with 5 ml of ethanol. The hydrogenation was carried out at 100° C., a constant pressure of 80 bar of pure $H_2$ and with intensive stirring for 24 hours. After completion of the reaction, 50 ml of diethyl ether were added, the catalyst complex was separated off by filtration, the filtrate was washed with aqueous sodium carbonate solution and the solvent was distilled off on a rotary evaporator. 11.1 g (96%) of 1-ethyl 8-methyl (S)-3-hydroxyoctanedioate (content: 95%) having an enantiomeric excess of 84% (chiral HPLC) were obtained.

What is claimed is:

1. Process for the preparation of compounds of the general formula I

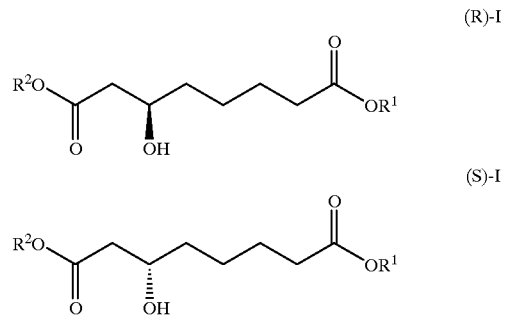

in which $R^1$ and $R^2$ are identical or different and are a $C_1$–$C_{20}$-alkyl group, $C_3$–$C_{20}$-cycloalkyl group, $C_7$–$C_{12}$-aralkyl group and/or mono- or binuclear aryl group, characterized in that a ketone of the formula IV

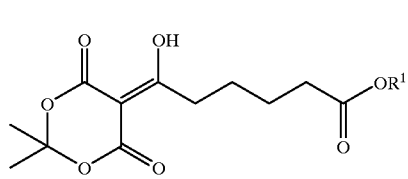

in which $R^1$ has the above meaning, is asymmetrically hydrogenated in the presence of a complex of ruthenium and an optically active phosphine as well as an alcohol $R^2OH$, in which $R^2$ has the above meaning.

* * * * *